United States Patent
Bao et al.

(10) Patent No.: US 9,834,540 B2
(45) Date of Patent: Dec. 5, 2017

(54) OMEPRAZOLE SODIUM SEMIHYDRATE AND PREPARATION METHOD THEREOF

(71) Applicants: TIANJIN UNIVERSITY, Tianjin (CN); HAINAN LINGKANG PHARMACEUTICAL CO., LTD, Haikou (CN)

(72) Inventors: Ying Bao, Tianjin (CN); Linggang Tao, Haikou (CN); Long Li, Tianjin (CN); Hongxun Hao, Tianjin (CN); Jun Lv, Haikou (CN); Baohong Hou, Tianjin (CN)

(73) Assignees: TIANJIN UNIVERSITY, Tianjin (CN); HAINAN LINGKANG PHARMACEUTICAL CO., LTD, Haikou (CN)

( * ) Notice: Subject to any disclaimer, the term of this patent is extended or adjusted under 35 U.S.C. 154(b) by 0 days.

(21) Appl. No.: 15/305,653

(22) PCT Filed: Nov. 20, 2015

(86) PCT No.: PCT/CN2015/095230
§ 371 (c)(1),
(2) Date: Oct. 20, 2016

(87) PCT Pub. No.: WO2016/155334
PCT Pub. Date: Oct. 6, 2016

(65) Prior Publication Data
US 2017/0044137 A1     Feb. 16, 2017

(30) Foreign Application Priority Data

Apr. 2, 2015   (CN) .......................... 2015 1 0154080

(51) Int. Cl.
*C07D 401/12* (2006.01)

(52) U.S. Cl.
CPC ........ *C07D 401/12* (2013.01); *C07B 2200/13* (2013.01)

(58) Field of Classification Search
CPC ..................................................... C07D 401/12
USPC ...................................................... 546/273.7
See application file for complete search history.

(56) References Cited

FOREIGN PATENT DOCUMENTS

| CN | 102285970 | * | 12/2011 |
| CN | 102321072 | * | 1/2012 |

OTHER PUBLICATIONS

Murakami et al., "Physico-chemical, etc.," Journal of Pharmaceutical and Biomedical Analysis 49 (2009) 72-80.*

* cited by examiner

*Primary Examiner* — Patricia L Morris
(74) *Attorney, Agent, or Firm* — CBM Patent Consulting, LLC

(57) ABSTRACT

It discloses Omeprazole Sodium semihydrate and preparation method thereof, wherein every mole of Omeprazole Sodium semihydrate contains 0.5 mole of water, and it has an X-ray diffraction pattern comprising characteristic peaks at diffraction angles 2θ of 6.26°±0.1°, 11.10°±0.1°, 12.20°±0.1°, 15.58°±0.1°, 16.02°±0.1°, 17.12°±0.1°, 19.08°±0.1°, 21.00°±0.1°, 22.68°±0.1°, 23.48°±0.1°, 24.08°±0.1°, 26.52°±0.1° and 28.08°±0.1°. A raw material of Omeprazole Sodium hydrate is added into an organic solvent, stirring for 2~9 hours at constant temperature of 25~60° C., thereafter Omeprazole Sodium semihydrate is provided after filtrating and drying.

6 Claims, 4 Drawing Sheets

OMEPRAZOLE SODIUM SEMIHYDRATE AND PREPARATION METHOD THEREOF

This application is the U.S. national phase of International Application No. PCT/CN2015/095230 filed on 20 Nov. 2015 which designated the U.S. and claims priority to Chinese Application Nos. CN201510154080.0 filed on 2 Apr. 2015, the entire contents of each of which are hereby incorporated by reference.

FIELD OF THE INVENTION

The present invention belongs to medical crystallization technology in chemical engineering field, and relates to Omeprazole Sodium semihydrate and its preparation method.

PRIOR ART

Omeprazole Sodium has a chemical name of 5-methoxy-2-[[(4-methoxy-3,5-dimethyl-2-pyridyl)methyl]sulfinyl)]-1H-benzoimidazole sodium salt, a molecular formula of $C_{17}H_{18}N_3NoaS$, a relative molecular mass of 367.4 and the following chemical structure:

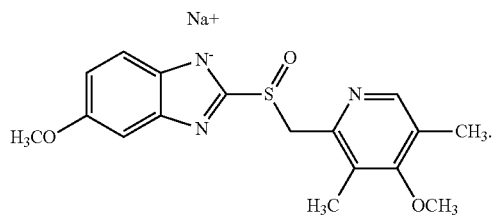 [SMILES: [Na+] ; COc1ccc2[n-]c(S(=O)Cc3ncc(C)c(OC)c3C)nc2c1]

Omeprazole Sodium is racemic mixture of a pair of reactive optical antipodes, reducing the secretion of gastric acid via the effect of high targeting, which makes it a special acid pump inhibitor in parietal cells. Omeprazole is lipo-soluble, which could be concentrated around the parietal cellular secretory canaliculus, and converted to active sulphonamide derivatives. Omeprazole Sodium has a more significant therapeutic effectiveness, a higher cure rate and a lower recurrence rate comparing to $H_2$-receptor blockers. All of these indicate the wide applications and large market potential of Omeprazole Sodium.

U.S. Pat. No. 4,738,974 A reports and prepares an Omeprazole Sodium hydrate containing 1 to 2 hydrones (water molecule). This hydrate has poor stability and high hygroscopicity, and its increased water content is obviously not convenient to quantitative packing in downstream preparation process, therefore not convenient to industrial applications. A preparation method of reacting Omeprazole with an alkali, dissolved-precipitating and cooling crystallization is used in this patent, providing Omeprazole Sodium hydrate and an amorphous mixture with low crystal purity because of the supersaturation and high precipitation rate in dissolved-precipitating process, and the operation takes a long time since it is conducted overnight.

WO 1999000380 A1 reports Omeprazole Sodium monohydrate (commercially available crystal form currently). The monohydrate has poor stability and low thermal decomposition temperature of 209.0° C. A preparation method of reacting Omeprazole with an alkali and crystallizing is used in this patent, in which two mixed solvents are necessary, and the crystallizing operation is time-consuming for required 10~24 hours, which leads to a low efficiency.

Therefore, it is necessary to develop an Omeprazole Sodium hydrate with obvious advantages, including simple preparation process, high yield, good thermal stability, excellent flowability and low hygroscopicity.

DETAILED DESCRIPTION OF THE INVENTION

The present invention discloses a novel solvate of Omeprazole Sodium, particularly discloses an Omeprazole Sodium semihydrate, which contains 0.5 mole of water in every mole of Omeprazole Sodium semihydrate and has the following structural formula (I):

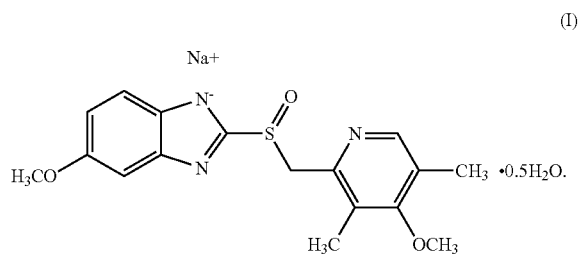 [SMILES: [Na+] ; COc1ccc2[n-]c(S(=O)Cc3ncc(C)c(OC)c3C)nc2c1]

Karl Fischer method is most faithful and accurate among various methods for water determination within substances, which has already been listed as a standard method for water determination within various substances, and accurate and reliable results will been got especially for organic compounds. After washing with acetone and drying, water content within Omeprazole Sodium semihydrate provided in the present invention is measured to be 2.28~2.45 wt. % by Karl Fischer method, which is same as the water content within Omeprazole Sodium semihydrate without washing with acetone. Since the theoretical water content within Omeprazole Sodium semihydrate is 2.39%, it could be confirmed that 0.5 crystal water (lattice water) is contained within every Omeprazole Sodium semihydrate provided in the present invention.

Omeprazole Sodium semihydrate provided in the present invention has an X-ray powder diffraction pattern comprising characteristic diffraction peaks at diffraction angles 2θ of 6.26°±0.1°, 11.10°±0.1°, 12.20°±0.1°, 15.58°±0.1°, 16.02°±0.1°, 17.12°±0.1°, 19.08°±0.1°, 21.00°±0.1°, 22.68°±0.1°, 23.48°±0.1°, 24.08°±0.1°, 26.52°±0.1° and 28.08°±0.1°, as shown in FIG. 1. Test conditions of X-ray powder diffraction are as follows: performing on a Rigaku D/max 2500 X-ray powder diffractometer (Rigaku Corporation, Japan), using CuKα radiation with light tube voltage of 40 kV and filament current of 300 mA, continuous scanning at a scanning step of 0.02°, a scanning speed of 8°/min and a scanning range of 2~50°.

It has been reported by lots of literatures that different solvates of the same substance with different crystal forms might has identical or partly identical X-ray powder diffraction pattern. Thus, it is necessary to provide another identification method to prove what is disclosed in the present invention is a novel hydrate, according to the "Guidance for quality control techniques and methods of pharmaceutical polymorphs".

Omeprazole Sodium semihydrate provided in the present invention has a Fourier transform infrared spectrum comprising characteristic absorption peaks at wave numbers of 3413.5±2, 3131.9±2, 2969.3±2, 2938.8±2, 2847.4±2, 2755.5±2, 1606.7±2, 1571.1±2, 1473.9±2, 1440.5±2, 1376.3±2, 1266.5±2, 1147.0±2, 1111.5±2, 1073.8±2, 1032.3±2, 942.3±2, 830.2±2, 802.6±2, 750.6±2 and 672.7±2 $cm^{-1}$, as shown in FIG. 2. Test conditions of Fourier transform infrared spectrum are as follows: performing on Nicolet, Nexus470 with potassium bromide tabletting.

DSC analysis results of Omeprazole Sodium semihydrate provided in the present invention suggest that it has a decomposing exothermic peak at 228.5±1° C., as shown in FIG. 3. The DSC data is obtained by analysis using a differential scanning calorimetry (DSC1/500, Mettler Toledo Corporation, Switzerland), and the analysis conditions are as follows: adding 10 mg of sample to a 40 μL Aluminum crucible, providing high-purity nitrogen as reaction gas and shield gas with a gas-flow rate of 50 mL/min and 20 mL/min, and raising the temperature at a rate of 10° C./min and a range of 25~300° C.

Said Omeprazole Sodium semihydrate has a rodlike shape and a main particle size of about 100 μm, as shown in microscope photographs of FIG. 4. The microscope photographs are obtained by observing and recording using polarizing microscope (OLYMPUS BX51, MicroPublisher 5.0 RTU).

In the preparation method of Omeprazole Sodium semihydrate provided in the present invention, a raw material of Omeprazole Sodium hydrate is added into an organic solvent, stirring for 2~9 hours at constant temperature of 25~60° C., filtrating and drying to provide Omeprazole Sodium semihydrate.

Said organic solvent is selected from one of n-propanol, n-butanol, s-butanol, formamide, N,N-dimethylformamide, methyl acetate, ethyl acetate, butyl acetate, n-heptane, chloroform, acetonitrile, tetrahydrofuran, acetone, butanone and methyl isobutyl ketone or a mixture thereof.

Said raw material of Omeprazole Sodium hydrate has an initial concentration of 0.015~0.12 g/mL.

The stirring way and stirring speed have no obvious influence on crystal transformation.

Omeprazole Sodium is liable to the formation of hydrate probably by hydrogen bonds between the oxygen atom in sulfinyl group and the water molecule. The specific organic solvent using in the present invention could interact with water molecule in the raw material of Omeprazole Sodium hydrate, partly dehydrate and joint two molecule of Omeprazole Sodium with one molecule of water. Additionally, the raw material of Omeprazole Sodium hydrate has a high solubility in these specific organic solvents, in which Omeprazole Sodium semihydrate has low solubility. Therefore, Omeprazole Sodium semihydrate with a high yield and a good form is provided in the present invention with the raw material of Omeprazole Sodium hydrate by using suitable solvent and preparing at appropriate concentration, temperature as well as time.

The preparation method of Omeprazole Sodium semihydrate provided in the present invention has advantages of simple operation, wash-free filter cake and low cost of solvent; high-speed crystallization, filtration and drying, low time consumption and high efficiency; without evaporation, and low energy consumption; high mole yield of not less than 95%; purity of the obtained Omeprazole Sodium semihydrate (calculated as anhydride) is about 100% by high performance liquid chromatography (HPLC), which conforms to the purity of 98~101.0% in the European pharmacopoeia.

More beneficial effects of the present invention are also reflected in the crystal form and crystal stability. Omeprazole Sodium semihydrate provided in the present invention has good crystal form, which is block-shaped and sole crystal form with smooth surface and low agglomeration rate, and it has an excellent flowability with carr index of less than 15%. The monohydrate reported in WO1999000380A1 has a poor flowability with can index of more than 41% as determined by the applicant. Omeprazole Sodium semihydrate provided in the present invention has a good thermal stability: DSC analysis suggests it has a thermal decomposition temperature of 228.5° C., which is much higher than the thermal decomposition temperature of 209.0° C. of Omeprazole Sodium monohydrate (as shown in FIG. 5). Thermal stability test results at 60° C. suggest that Omeprazole Sodium semihydrate provided in the present invention has a stable crystal form, and it does not make any significant change (whose X-ray diffraction pattern is as shown in FIG. 6), with a 10-day weight changing rate of within 2.2%, which is smaller than the weight changing rate of 4.8% of Omeprazole Sodium monohydrate, so it has a better stability (as shown in Tab. 1). Omeprazole Sodium semihydrate provided in the present invention has a lower hygroscopicity compared with that of Omeprazole Sodium monohydrate (as shown in Tab. 2). Therefore, Omeprazole Sodium semihydrate provided in the present invention is better than Omeprazole Sodium monohydrate in aspects of thermal stability, flowability and moisture resistance, therefore has broader application prospect.

TABLE 1

Stability comparison at 60° C. between Omeprazole Sodium semihydrate provided in the present invention and Omeprazole Sodium monohydrate.

| Time | Weight of Omeprazole Sodium monohydrate/g | Weight changing rate/% | Weight of Omeprazole Sodium semihydrate/g | Weight changing rate/% |
|---|---|---|---|---|
| 0 day | 9.6761 | 0 | 9.5852 | 0 |
| 5 day | 9.3859 | 3.0 | 9.4826 | 1.1 |
| 10 day | 9.2108 | 4.8 | 9.3790 | 2.2 |

Note:
according to "Guidance for stability testing techniques of chemical drugs", the sample is added to an airtight, clean container at 60° C. for 10 days, and weighed regularly.

TABLE 2

Hygroscopicity comparison at 40° C. between Omeprazole Sodium semihydrate provided in the present invention and Omeprazole Sodium monohydrate.

| Relative humidity/% | Weight changing rate of Omeprazole Sodium monohydrate/% | Weight changing rate of Omeprazole Sodium semihydrate/% |
|---|---|---|
| 0 | 0 | 0 |
| 5 | 0.002 | 0.001 |
| 10 | 0.01 | 0.004 |
| 15 | 0.02 | 0.01 |
| 20 | 0.03 | 0.02 |
| 25 | 0.04 | 0.02 |
| 30 | 0.04 | 0.03 |
| 35 | 0.04 | 0.03 |
| 40 | 0.04 | 0.03 |
| 45 | 0.38 | 0.14 |
| 50 | 0.46 | 0.17 |
| 55 | 0.56 | 0.28 |
| 60 | 0.71 | 0.37 |
| 65 | 0.95 | 0.45 |

TABLE 2-continued

Hygroscopicity comparison at 40° C. between
Omeprazole Sodium semihydrate provided in the present
invention and Omeprazole Sodium monohydrate.

| Relative humidity/% | Weight changing rate of Omeprazole Sodium monohydrate/% | Weight changing rate of Omeprazole Sodium semihydrate/% |
|---|---|---|
| 70 | 1.15 | 0.53 |
| 75 | 1.49 | 0.69 |

Note:
the sample is added to a dynamic vapor sorption at 40° C., and the weight is recorded when weight changing is less than 0.01 g within 3 hours.

Toxic responses of Omeprazole Sodium semihydrate obtained in the present invention suggest it has an improved toxicity than that of currently existing Omeprazole Sodium or monohydrate thereof; both drug mutation test and reproductive toxicity test show negative results, and cancer metastasis is not found in Carcinogenic test.

EMBODIMENTS OF THE INVENTION

The present invention is further illustrated by the following examples, while it cannot be understood as the scope defined by above main body of the present invention is limited to the following examples. Technology implemented based on the above-identified content of the present invention all belong to the scope of the present invention.

Example 1

Figure 1:
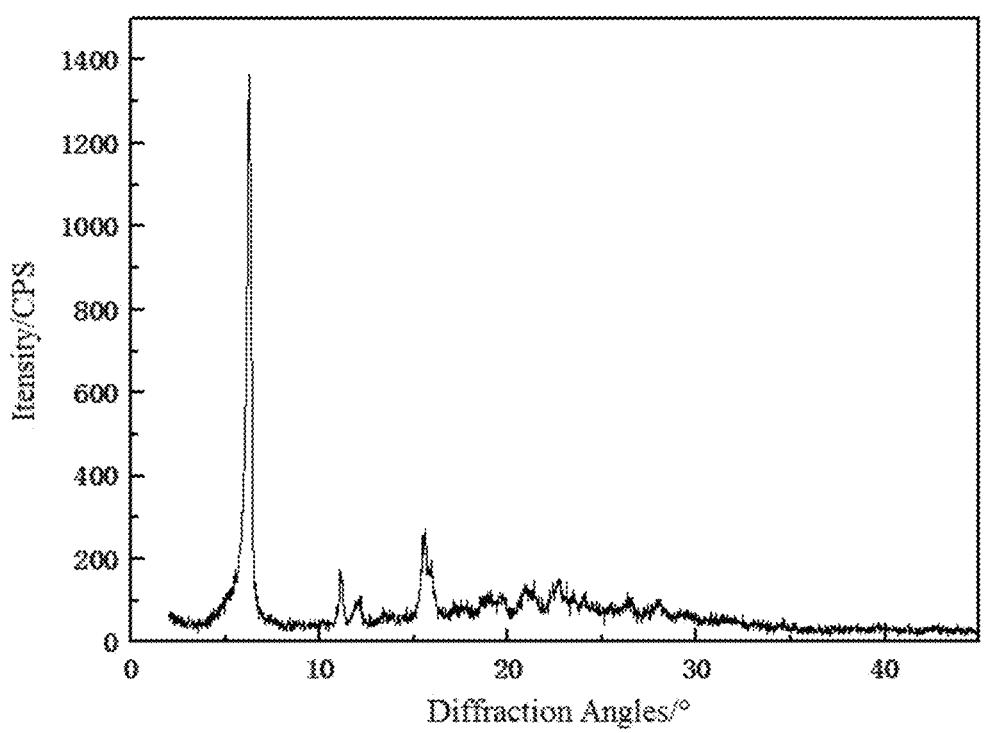
FIG. 1 shows the X-ray powder diffraction pattern of Omeprazole Sodium semihydrate.
Figure 2:
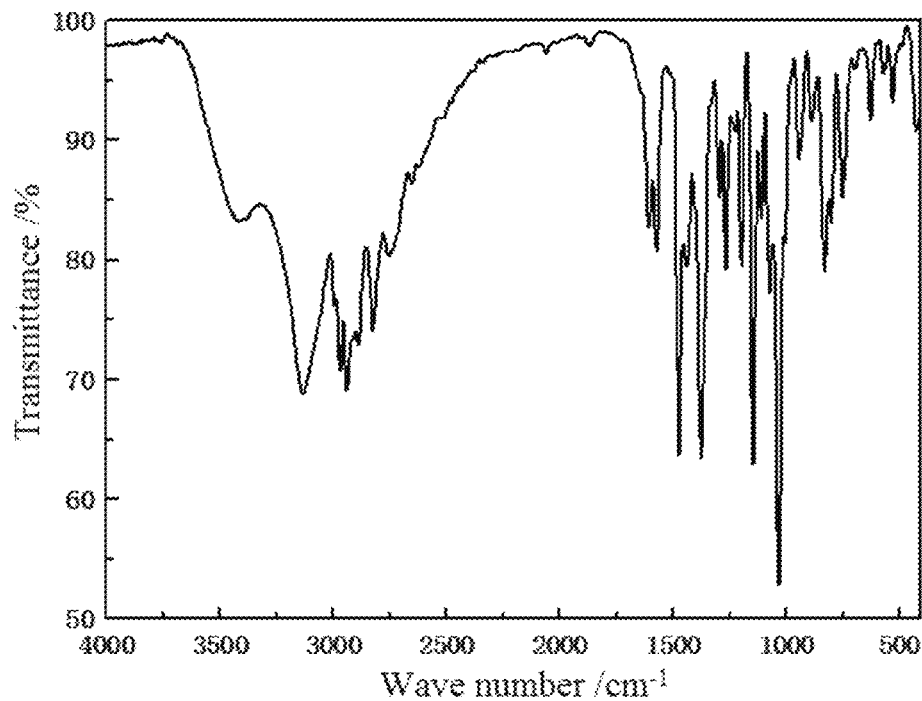
FIG. 2 shows the Fourier transform infrared (FT-IR) spectrum of Omeprazole Sodium semihydrate.
Figure 3:
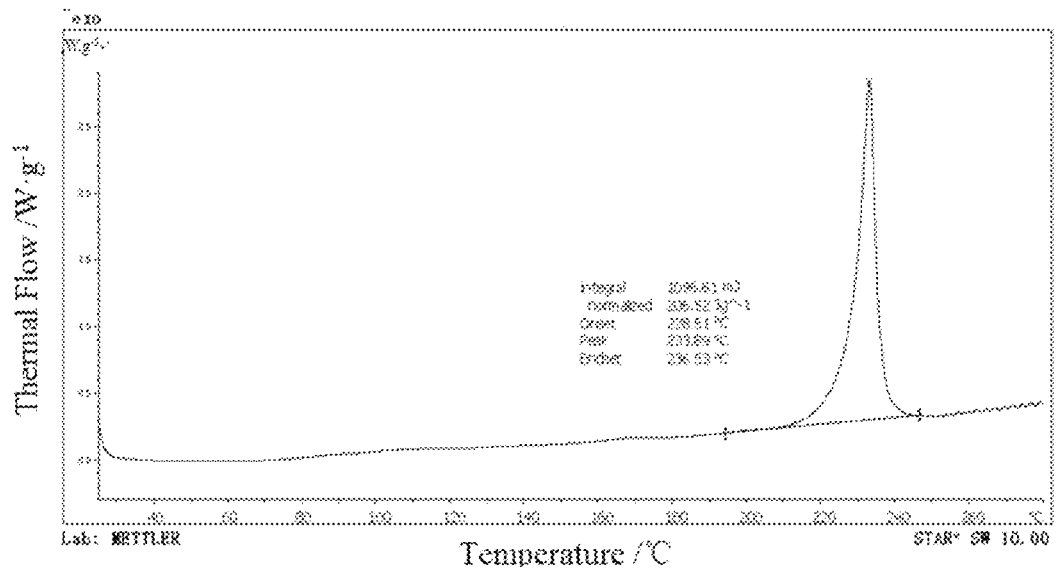
FIG. 3 shows the differential scanning calorimetry (DSC) thermogram of Omeprazole Sodium semihydrate.
Figure 4:
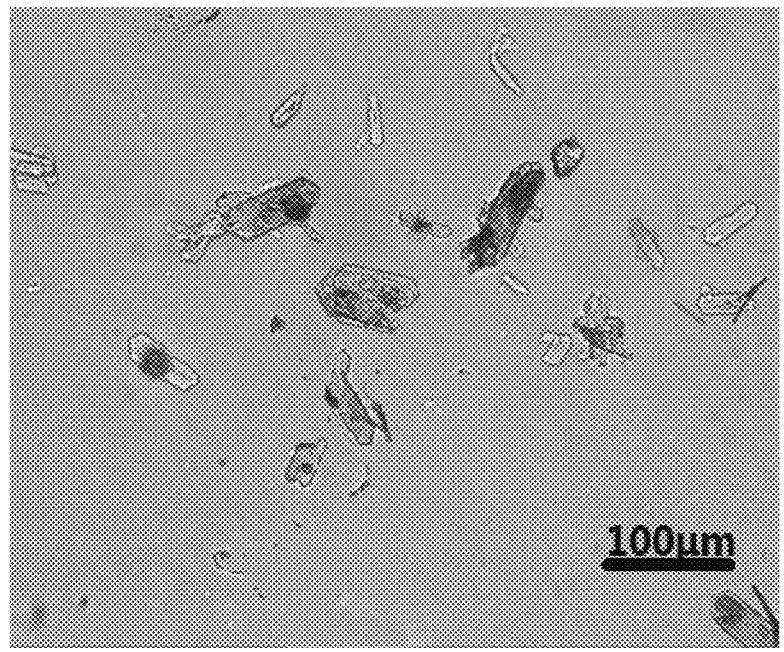
FIG. 4 shows the micrograph of Omeprazole Sodium semihydrate.
Figure 5:
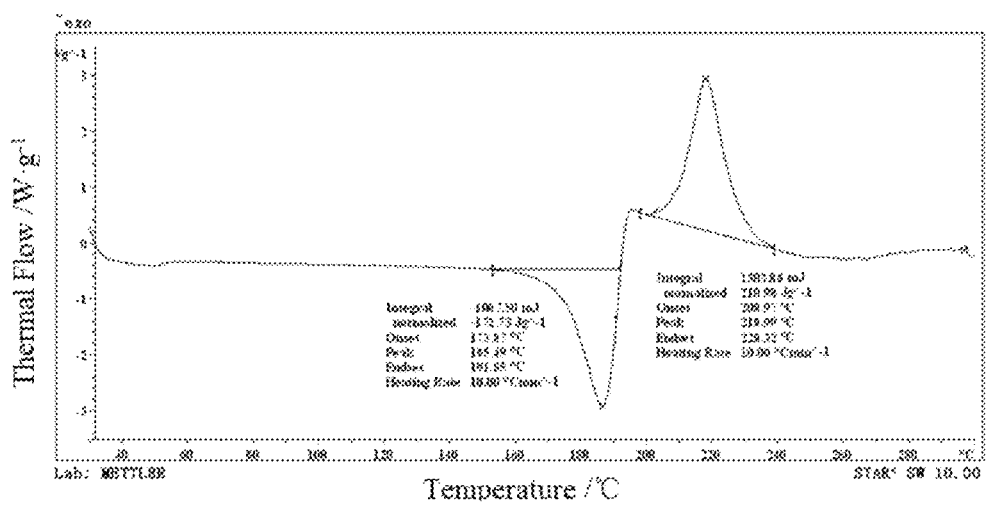
FIG. 5 shows the differential scanning calorimetry (DSC) thermogram of Omeprazole Sodium monohydrate.
Figure 6:
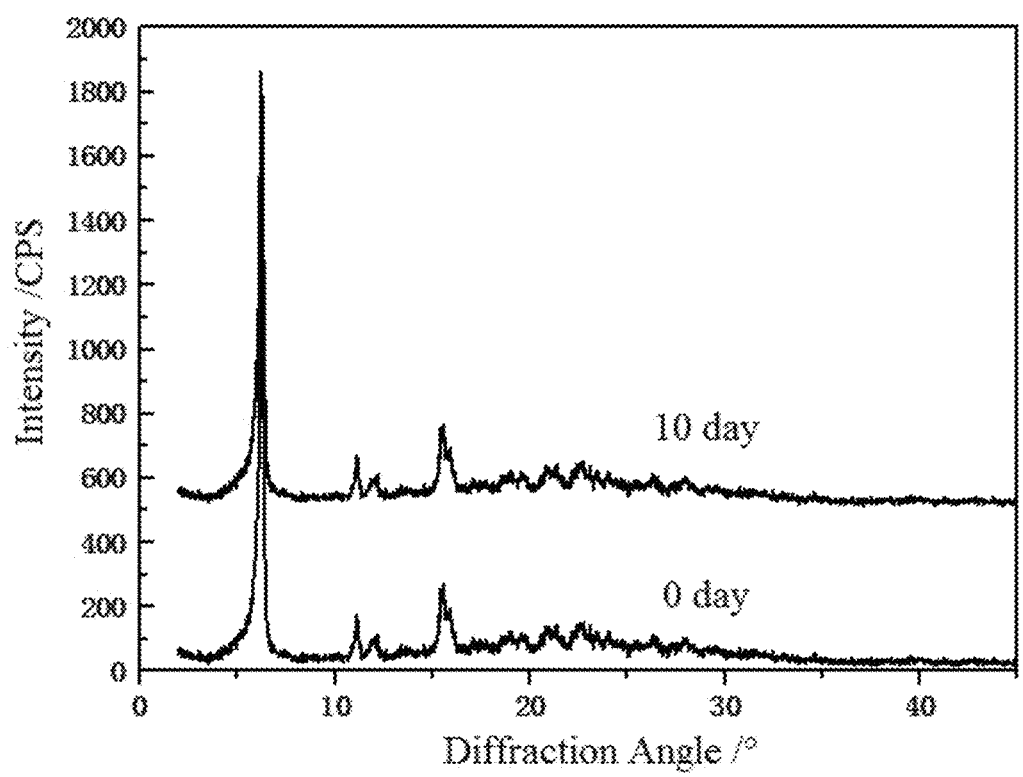
FIG. 6 shows the contrasting X-ray powder diffraction patterns of Omeprazole Sodium semihydrate being put at a temperature of 60° C. before and after 10 days.

0.45 g of Omeprazole Sodium monohydrate, 20 mL of ethyl acetate and 10 mL of s-butanol were added to a crystallizer, and the mixture was stirred at a temperature of 35° C. and a speed of 200 r/min for 2 hours, followed by filtrating and drying to provide 0.42 g of Omeprazole Sodium semihydrate with a mole yield of 95.6% and a HPLC purity of 99.8%. The product had same X-ray powder diffraction pattern as FIG. 1, same solid Fourier transform infrared spectrum as FIG. 2, and DSC decomposition temperature of 227.5° C. (as shown in FIG. 3). It had main crystal particle size of 92 μm without coalescencing, and the carr index was 14.3% which suggested a good flowability. It maintained as white crystal after being deposited at high temperature of 60° C. without making any significant changes in the X-ray powder diffraction pattern (as shown in FIG. 6), thermal stability test at 60° C. suggested that it had good thermal stability with a 10-day weight changing rate of 2.4%. After being deposited under the condition of 40° C. and relative humidity 75% for 3 days, weight changing rate of the product was 0.68%, which suggested it had low hygroscopicity.

Example 2

2.40 g of Omeprazole Sodium monohydrate and 20 mL of methyl isobutyl ketone were added to a crystallizer, and the mixture was mechanically stirred at a temperature of 60° C. and a speed of 300 r/min for 7 hours, filtrated and dried at a temperature of 35° C. and a vacuum degree of 0.05 MPa to provide 2.27 g of Omeprazole Sodium semihydrate with a mole yield of 96.8% and a HPLC purity of 100.2%. The product had an X-ray powder diffraction pattern comprising characteristic peaks at diffraction angles 2θ of 6.34°, 11.18°, 12.26°, 15.58°, 16.02°, 17.06°, 19.12°, 21.04°, 22.66°, 23.52°, 24.10°, 26.44° and 28.04°, and a solid Fourier transform infrared spectrum comprising characteristic peaks at wave numbers of 3414.5, 3132.1, 2969.9, 2939.8, 2846.9, 2756.5, 1607.7, 1571.9, 1474.5, 1441.5, 1377.3, 1266.0, 1147.8, 1112.3, 1072.8, 1032.9, 941.3, 830.7, 803.4, 751.1 and 673.2 $cm^{-1}$, and a DSC decomposition temperature of 229.2° C. It had main crystal particle size of 95 μm without coalescencing, and the can index was 13.9% which suggested a good flowability. It maintained as white crystal after being deposited at high temperature of 60° C. without making any significant changes in the X-ray powder diffraction pattern, thermal stability test at 60° C. suggested that it had good thermal stability with a 10-day weight changing rate of 2.5%.

Example 3

3.00 g of Omeprazole Sodium hydrate (with water content of 7.02%), 10 mL of tetrahydrofuran, 10 mL of formamide and 10 mL of butanone were added to a crystallizer, and the mixture was mechanically stirred at a temperature of 25° C. and a speed of 600 r/min for 9 hours, filtrated and dried at a temperature of 30° C. and a vacuum degree of 0.1 MPa to provide 2.78 g of Omeprazole Sodium semihydrate with a mole yield of 97.4% and a HPLC purity of 100.0%. The product had an X-ray powder diffraction pattern comprising characteristic peaks at diffraction angles 2θ of 6.28°, 11.16°, 12.16°, 15.62°, 16.02°, 17.02°, 19.10°, 21.00°, 22.60°, 23.44°, 24.16°, 26.42° and 28.02°, and a solid Fourier transform infrared spectrum comprising characteristic peaks at wave numbers of 3413.0, 3132.3, 2968.7, 2938.1, 2846.8, 2754.6, 1605.4, 1572.1, 1474.6, 1441.5, 1375.8, 1266.2, 1146.8, 1111.0, 1074.2, 1032.9, 942.8, 831.2, 803.6, 751.5 and 671.7 $cm^{-1}$, and a DSC decomposition temperature of 229.5° C. It had main crystal particle size of 100 μm without coalescencing, and the carr index was 14.7% which suggested a good flowability. It maintained as white crystal after being deposited at high temperature of 60° C. without making any significant changes in the X-ray powder diffraction pattern, thermal stability test at 60° C. suggested that it had good thermal stability with a 10-day weight changing rate of 2.4%.

Toxicity Tests:

The Omeprazole Sodium semihydrate obtained in the present invention was tested by toxic responses tests, drug mutation tests, reproductive toxicity tests and carcinogenic tests (taking Omeprazole Sodium semihydrate obtained in Example 1 for example).

In the long-term treatment research of Omeprazole in rats, cell increase and benign tumour were observed in stomach ECL cells, which resulted from persistent hypergastrinemia inhibited by gastric acid. Intravenous LDLo (lowest published lethal dose) in dogs was 500 mg/kg, and intravenous $LD_{50}$ (median lethal dose) in rats was 302 mg/kg. Intravenous $LD_{50}$ in mice was 82.8 mg/kg, and oral $LD_{50}$>2000 mg/kg.

It had no influence on reproductive performance of male and female rats at an oral dosage of 138 mg/kg/day (about 34 times of human dose based on body surface area 40 mg/kg/day).

By the long-term toxicity test in which rats were treated with Omeprazole persistently at a dosage of 140 mg/kg/day for 1~6 months, it could be observed that the liver and kidney increased in weight without histologic changes.

Treating rats and dogs with Omeprazole persistently at a dosage of 14~140 mg/kg/day for 3 months could induce hypergastrinemia (1000~5000 pg/ml), which was feedback response caused by reduction in gastric acid secretion, and could be recovered after drug withdrawal.

Both of drug mutation test and reproductive toxicity test gave negative results.

By the carcinogenic test in rats within 24 months (persistently treated), it was discovered that enterochromaffin-like cell hyperplasia in gastric mucosa was caused by hypergastrinemia, and carcinogenesis occurred without cancer metastasis.

The present invention discloses and provides an Omeprazole Sodium semihydrate and preparation method thereof, with referring to the present invention, the skilled person in the art could make it implemented by altering materials and process parameter properly. Method and product of the present invention have already been illustrated by preferable embodiments, it will be apparent for related technicians to make proper changes, modifications and combinations according to the method and product provided by the present invention to achieve technology realization in the present invention, without deviating from the content, spirit and scope of the present disclosure. Especially, all of the similar replacements and modifications are obvious for those skilled in the art, which will be seen to fall within the spirit, scope and content of the present invention.

What is claimed is:

1. A crystallized omeprazole sodium semihydrate having a molecular formula $C_{17}H_{18}N_3NaO_3S0.5H_2O$, a structural formula shown as follows:

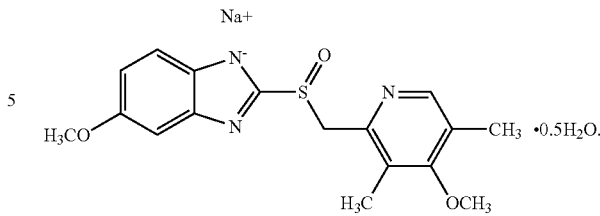

and an X-ray powder diffraction peaks (expressed in degree 2θ) at 6.26°±0.1°, 11.10°±0.1°, 12.20°±0.1°, 15.58°±0.1°, 16.02°±0.1°, 17.12°±0.1°, 19.08°±0.1°, 21.00°±0.1°, 22.68°±0.1°, 23.48°±0.1°, 24.08°±0.1°, 26.52°±0.1° and 28.08°±0.1°.

2. The crystallized omeprazole sodium semihydrate according to claim 1, wherein the crystallized omeprazole sodium semihydrate has an infrared spectrum with characteristic absorption peaks at wave numbers of 3413.5±2, 3131.9±2, 2969.3±2, 2938.8±2, 2847.4±2, 2755.5±2, 1606.7±2, 1571.1±2, 1473.9±2, 1440.5±2, 1376.3±2, 1266.5±2, 1147.0±2, 1111.5±2, 1073.8±2, 1032.3±2, 942.3±2, 830.2±2, 802.6±2, 750.6±2 and 672.7±2 $cm^{-1}$.

3. The crystallized omeprazole sodium semihydrate according to claim 1, wherein the crystallized omeprazole sodium semihydrate has a differential scanning calorimetric (DSC) thermogram with a decomposing exothermic peak at 228.5±1° C.

4. A method for preparing Omeprazole Sodium semihydrate according to claim 1, characterized in that: adding a raw material of Omeprazole Sodium hydrate into an organic solvent, stirring for 2~9 hours at constant temperature of 25~60° C., filtrating and drying to provide Omeprazole Sodium semihydrate.

5. The method according to claim 4, characterized in that, said organic solvent is selected from one of n-propanol, n-butanol, s-butanol, formamide, N,N-dimethylformamide, methyl acetate, ethyl acetate, butyl acetate, n-heptane, chloroform, acetonitrile, tetrahydrofuran, acetone, butanone and methyl isobutyl ketone or a mixture thereof.

6. The method according to claim 4, characterized in that, said raw material of Omeprazole Sodium hydrate has an initial concentration of 0.015~0.12 g/mL.

* * * * *